United States Patent [19]

Emmett

[11] 4,018,220
[45] Apr. 19, 1977

[54] METHOD OF INSERTION FOR INTRAUTERINE DEVICE OF C OR OMEGA FORM WITH TUBULAR INSERTER

[75] Inventor: Lionel C. R. Emmett, Kingston-upon Thames, England

[73] Assignee: Lionel C. R. Emmett, Surrey, England

[22] Filed: Feb. 23, 1976

[21] Appl. No.: 660,679

Related U.S. Application Data

[62] Division of Ser. No. 489,982, July 19, 1974, Pat. No. 3,973,560.

[52] U.S. Cl. .............................. 128/130; 128/260
[51] Int. Cl.² ............................................ A61F 5/46
[58] Field of Search ............... 128/130, 127, 260

[56] References Cited

UNITED STATES PATENTS

| 1,896,071 | 2/1933 | Clark | 128/130 |
|---|---|---|---|
| 3,200,815 | 8/1965 | Margulies | 128/130 |
| 3,306,286 | 2/1967 | Ahmed | 128/130 |
| 3,364,927 | 1/1968 | Robinson | 128/130 |
| 3,374,788 | 3/1968 | Rosenthal | 128/130 |
| 3,382,869 | 5/1968 | Rigney et al. | 128/130 |
| 3,397,690 | 8/1968 | Majzlin | 128/130 |
| 3,457,915 | 7/1969 | Eshelman | 128/130 |
| 3,467,088 | 9/1969 | Robinson | 128/130 |
| 3,492,990 | 2/1970 | Clarke | 128/130 |
| 3,515,132 | 6/1970 | McKnight | 128/130 |
| 3,516,403 | 6/1970 | Cournut | 128/130 |
| 3,545,439 | 12/1970 | Duncan | 128/130 |
| 3,563,235 | 2/1971 | Zipper | 128/260 X |
| 3,645,265 | 2/1972 | Majzlin | 128/130 |
| 3,777,748 | 12/1973 | Abramson | 128/130 |
| 3,810,456 | 5/1974 | Karman | 128/130 |
| 3,845,770 | 11/1974 | Theeuwes et al. | 128/130 |

FOREIGN PATENTS OR APPLICATIONS

532,437   9/1931   Germany .......................... 128/127

OTHER PUBLICATIONS

Intrauterine Contraceptive Devices, MIT, Jan. 1971, pp. 23 & 40, Excerpta Medica–International Congress, Series No. 54–1962, (Tietze & Lewit, Eds.).

Primary Examiner—Lawrence W. Trapp
Attorney, Agent, or Firm—Strauch, Nolan, Neale, Nies & Kurz

[57] ABSTRACT

An intrauterine contraceptive device made from plastic having a C-shape or Omega-shape to enable it to lie in the uterine cavity. Lines of predetermined length are attached at one of their ends respectively to enlargement portions of the terminal ends of the device and with their other ends fastened by a plastic bead and aid in insertion, removal and as a telltale marker. The device can include a metallic contraceptive material such as copper. One embodiment uses copper wire, which can be of selected different diameter, wound on the body of the device and retained against slippage by serrations on the body. A tubular inserter with appropriate grips and a cervical abutment flange is used to receive the IUD in elongated deformation. The device is slipped through the tubular inserter by a plunger and as the IUD emerges from the upper end of the tube, strain on one of the lines caused by abutment of the bead on the lower end of the tube positively bows and pulls the emerging IUD into a substantially circular configuration within the plane of the fundal cavity, the inserter having been appropriately oriented during the preliminary insertion steps.

7 Claims, 17 Drawing Figures

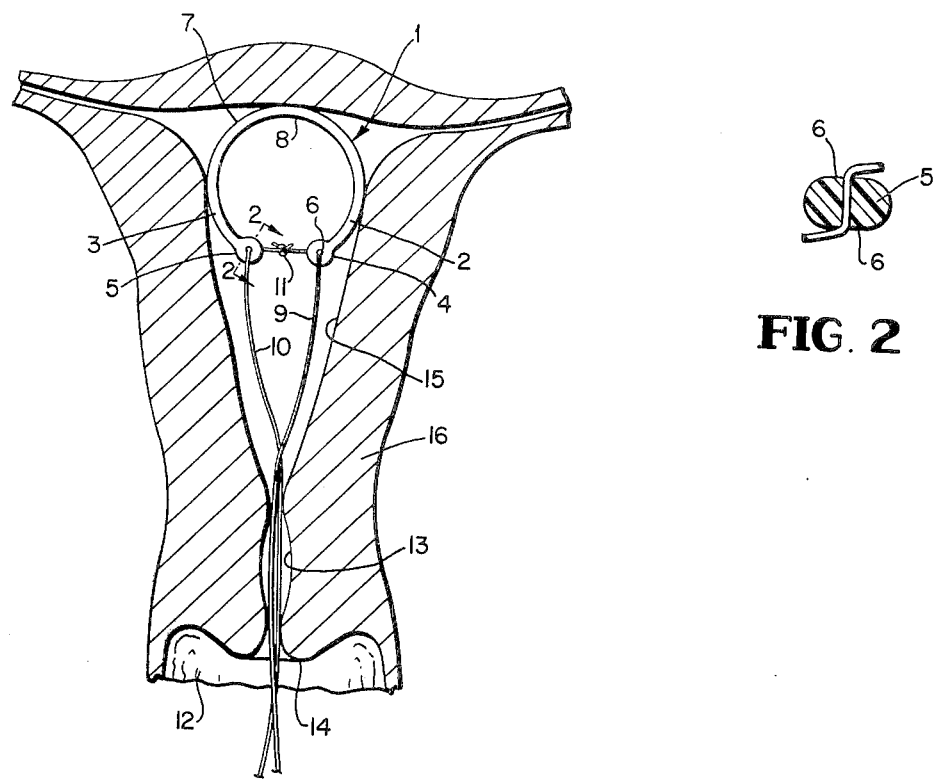
FIG. 1
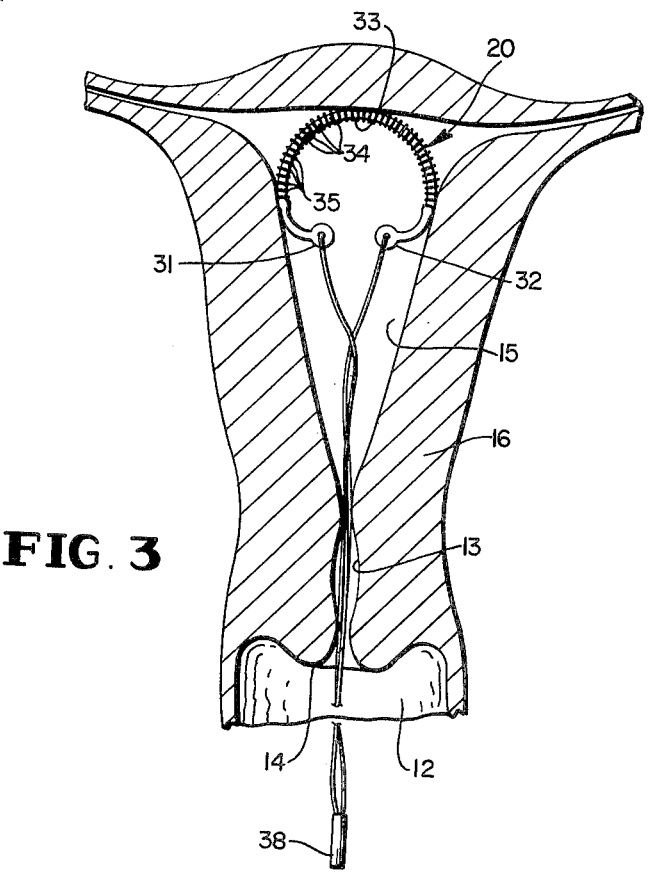
FIG. 2
FIG. 3

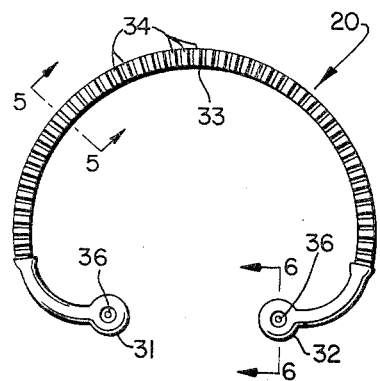
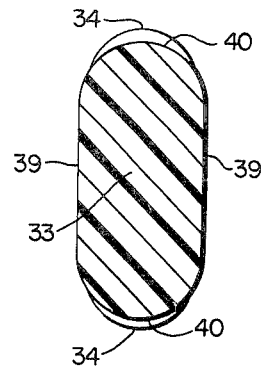
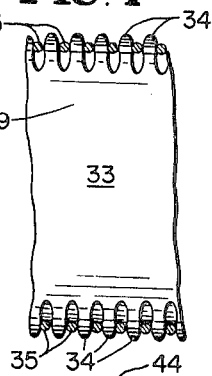
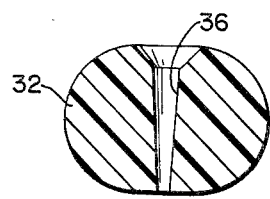
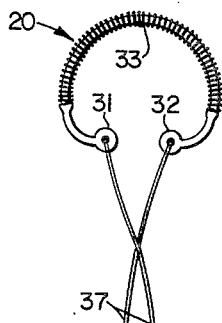
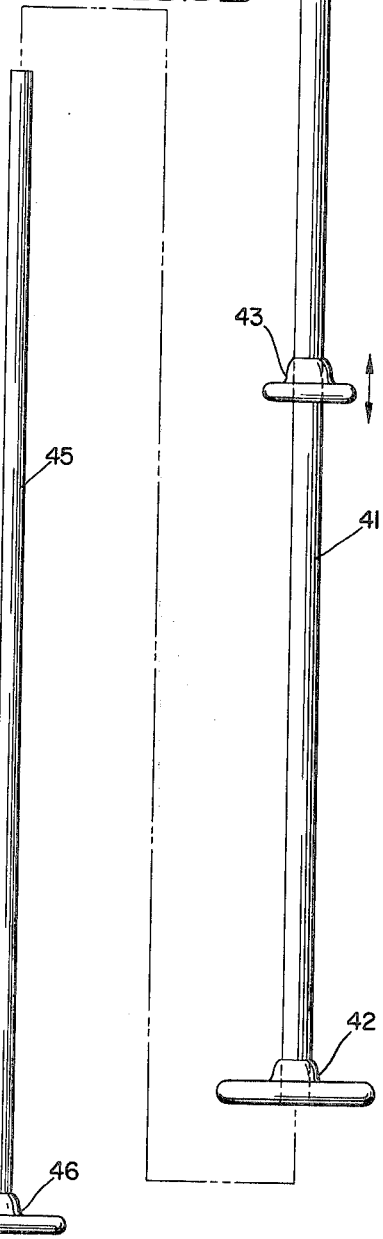
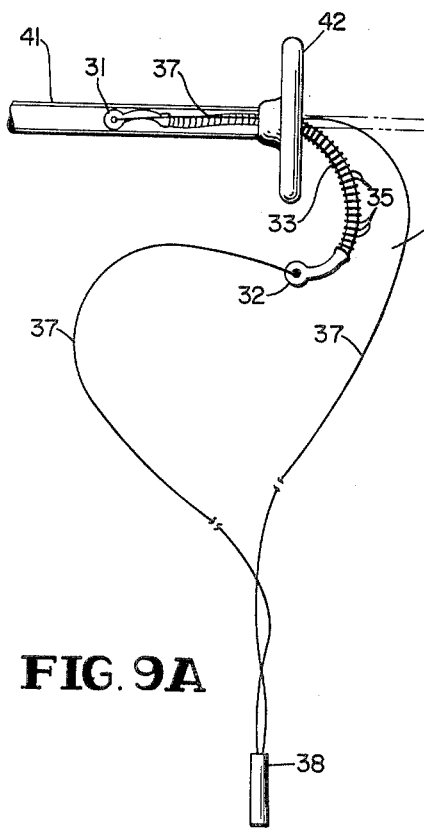

METHOD OF INSERTION FOR INTRAUTERINE DEVICE OF C OR OMEGA FORM WITH TUBULAR INSERTER

CROSS-REFERENCE TO RELATED APPLICATION

This application is a division of application Ser. No. 489,982 filed July 19, 1974 and now U.S. Pat. No. 3,973,560.

BACKGROUND OF THE INVENTION

Contraception with a foreign body in the uterine cavity of a woman — the intrauterine contraceptive device, commonly known as an IUD — has been practiced by the medical profession with an increasing measure of success. Thus the pregnancy rate with an IUD in position can be at least as low as 1.4%.

One proposed IUD is in the form of a zig-zag, others are T-shaped, bow-shaped, coiled and closed perimeters such as O-shapes.

SUMMARY OF THE INVENTION

According to one aspect of the invention this invention provides a contraceptive device comprising a substantially C-, omega-, or triangular shaped device which is adapted to lie in the uterine cavity.

According to a further aspect of the invention there is provided a contraceptive device comprising a substantially C-, omega- or triangular shaped member which is adapted to lie in the uterine cavity, and includes a metallic contraceptive agent which can comprise at least a part of the surface area of the IUD.

According to a still further aspect of the invention there is provided an intrauterine device as hereinbefore defined including an inserter for the insertion of the IUD in the fundal region of the uterine cavity, the inserter comprising a hollow tube of sufficient internal diameter to accommodate the device when said device is substantially straightened out. An external slidable flange on the hollow tube extends substantially transversely thereof and is arranged with respect to a delivery end thereof that a desired position of insertion of the device into the uterus can be determined.

According to a still further aspect of the invention there is provided a method of insertion of an intrauterine device as hereinbefore defined using an inserter as hereinbefore defined, the method comprising straightening the device and inserting it into the hollow tube and then inserting the plunger into the tube, inserting the tube through the cervical canal into the uterus until the slidable flange rests against the cervical os, fully inserting the plunger into the tube to transfer the device into the uterine cavity, removing the plunger, drawing the ends of the device together, by exerting traction on a bead which connects the threads to the device, separating the bead from the threads, and then withdrawing the inserter and trimming the threads at the os cervix.

Intrauterine devices and the inserter embodying the invention are diagrammatically illustrated, by way of example, in the accompanying drawings, in which:

FIG. 1 shows a longitudinal section through a uterus with one embodiment of the intrauterine device in position;

FIG. 2 is a cross-section taken on line 2—2 of FIG. 1;

FIG. 3 is a longitudinal section through a uterus showing a second embodiment of the intrauterine device in position;

FIG. 4 is an enlarged elevation view of the second form of the device;

FIG. 5 is a section taken on line 5—5 of FIG. 4;

FIG. 6 is a section taken on line 6—6 of FIG. 4;

FIG. 7 shows, on an enlarged scale, an elevation of part of the surface of the device of FIG. 4;

FIG. 8A shows an elevation of the second form of the device before insertion;

FIG. 8B shows an elevation of an inserter including tube and plunger;

FIG. 9A shows the initial insertion of the device into the inserter;

DESCRIPTION

Figure 9B:
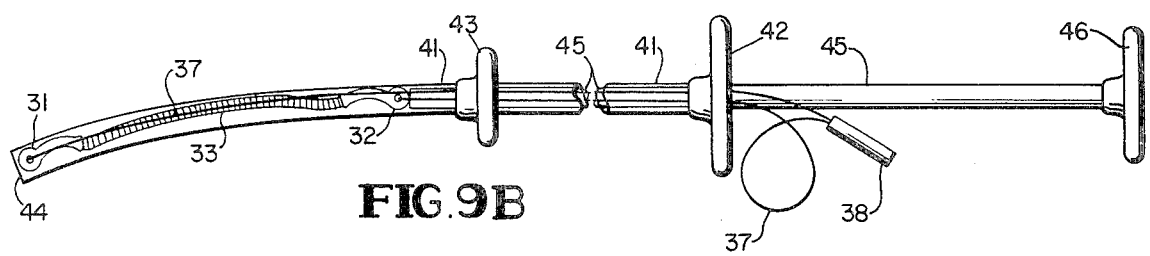
FIG. 9B shows the device placed fully in the inserter.

As shown in FIGS. 1 and 2 of the accompanying drawings, one embodiment of an intra-uterine device comprises a substantially C-shaped member 1, arms 2 and 3 of which are each rounded and enlarged at the ends to form nodules or enlarged heads 4 and 5. Opposite sides or surfaces 6 of the nodules are flattened (FIG. 2) to provide a pair of substantially parallel planar surfaces.

As shown, both nodules 4 and 5 are of identical size. In a modification, (not shown), one nodule may have a larger diameter than the other, for example, it may have a diameter 1 mm greater than that of the other.

The body of the member 1 is substantially oval in cross-section, one surface 7, the other surface as seen in FIG. 1, having a smaller radius of curvature than the other surface 8, the inner surface as seen in FIG. 1.

The outer surface 7 will thus have a curved or domed appearance while the inner surface 8 has a flattened appearance.

The IUD 1 is moulded from a pharmaceutical grade of plastics material which is resilient and has the property of having an elastic memory so that when deformed it substantially returns to its moulded shape. A suitable material is polypropylene. Another is one comprising 80% of polyethylene and 20% Barium sulphate.

There is a hole through each nodule 4 and 5. Nylon threads 9 and 10 of approximately 10 lbs. breaking strain are passed through the holes and are knotted together at 11. Alternatively the threads are not joined together but are secured, as by a knot on the inner side of the respective nodule.

There may be a close fitting copper sleeve on the body of the device between the nodules 4 and 5.

The distance between the nodules 4 and 5 is of the order of 5 to 7 mm.

The device 1 may be of various diameters, for example 23 mm, 25 mm, 27 mm and 29 mm.

In use, the patient is prepared and the (sterile) device is straightened out and one of the nodules, say nodule 4, is inserted into a fixed flange end of a (sterile) tubular inserter (FIG. 9) having a bore with cross-sectional configuration corresponding substantially to that of a nodule 4 and a size such that the nodule 4 has a close sliding fit in the bore, the flat sides 6 of the nodule 4 being parallel to the corresponding flat sides of the bore. The device 1 is then fed into the bore and a plunger is inserted into the loaded bore. The inserter is then introduced through the vagina 12 upwards into the cervical canal 13 until a positionable flange 43 on the body of the inserter rests against the cervix 14 and the inner end of the inserter lies at or near the fundal cavity 15 of the uterus 16. The inserter is then withdrawn about 1 cm and the plunger is pushed upwardly so that the device 1 is pushed out of the bore, and starting to return to its C-shape as it gradually exits from the inserter tube. When the plunger is withdrawn fully, the threads 9 and 10 extend through the cervical canal 13 into the vagina 12 a distance of about 5 mm, and the device takes up the C-shape in which it is moulded. During insertion, the flat sides of the nodules 4 and 5 prevent any twisting of the device in the bore of the inserter so that the device takes up the desired position in the uterus (shown in FIG. 1). As the front and rear walls of the uterus touch, the device is maintained in the desired position, while the resilience of the body of the device allows it to alter shape to accommodate contractions in the uterus. The rounded ends of the arms prevent damage to the walls of the uterus, while the resilience of the device and its simple configuration ensure that it stays in place in the uterus without being permanently deformed.

The device 1 is simply removed. One of the threads 9 or 10 is pulled downwardly and the device 1 follows, one of the nodulus 4 or 5 passing down through the cervical canal 13 followed by the remainder of the device, which straightens out as it passes downwardly through the canal.

Referring now to FIGS. 3 to 15, there is shown a second and preferred intrauterine contraceptive device 20 of C- omega-, or triangular shaped in which two enlarged heads 31 and 32 are integral with and connected by a U-shaped yoke or member 33 on which there are surface serrations 34 (FIG. 3). The serrations act as guides for a single continuous metal, for example copper wire 35 which is wound round the member 33. The wire is loosely wound around the member 33 so as not to interfere with the flexibility of the device. Further, the serrations keep the wire in position and prevent it from "bunching" when the device is being loaded into an inserter (described hereinafter). The opposite ends of the wire are embedded in the body 33 of the device 20 so as not to become loose in the uterine cavity. The device 20 is also made from plastics material, suitably from high quality pharmaceutical grade polypropylene which, after moulding in the shape shown, can be "straightened", whereafter on release the device will return to its original C- or omega-shape. The device 20 thus has an elastic memory. Each head has a counter-sunk tapered bore 36 therethrough. Two nylon threads 37 are secured by knotting one end and pulling the knot into its associated bore 36, the other ends of the two threads being secured in a cylindrical bead 38 at a determined distance from the heads, that distance or length of each thread being greater than the length of the inserter tube by approximately the dimension between the heads 31 and 32.

The available surface area of the copper wire can be varied between 200 sq. mm and 450 sq. mm by using wire of larger or smaller diameter as preferred.

The member 33 is substantially ellipsoidal in cross-section having a pair of opposite planar boundary surfaces 39 which are joined or connected by convex surfaces 40.

The device 20 may have a transverse width of 23 MM, a depth of 21 MM, and a gap of approximately 3 MM between the heads 31 and 32. The dimensions of the member 33 in such a device may be depth 2 MM and width 1.5 MM, the size of the heads being 2.5 × 2 MM.

Other sizes of the devices may have corresponding dimensions as follows:

1. 27 MM, 23 MM, 7 MM, 3 MM, 1.5 MM, 4 × 3 MM
2. 31 MM, 25 MM, 11 MM, 3 MM, 2 MM, 4 × 3 MM
3. 35 MM, 27 MM, 15 MM, 3.5 MM, 2 MM, 5 × 4 MM.

The device 20 is inserted in the uterus using an inserter which comprises a hollow tube 41 having a fixed flange providing a finger grip 42 at a posterior end. Intermediate the length of the inserter tube there is slidable flange 43, which can be moved to vary as desired the distance between the flange and an anterior end 44 of the inserter. The inserter is provided with a removable plunger 45 which can be inserted in the tube in a telescopic manner. The plunger 45 has a grip 46.

The device, inserter and plunger are put up in a sterilized pack (not shown), with which is included instructions for insertion.

Figure 10:
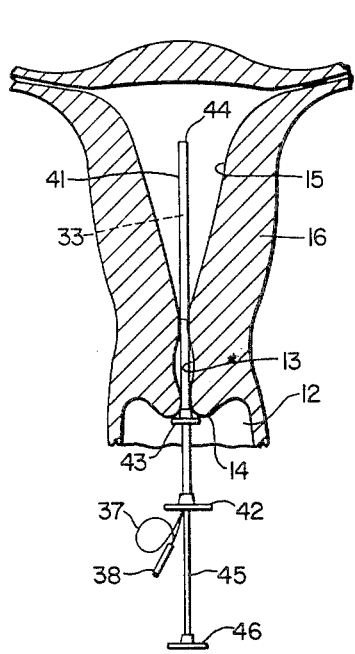
FIGS. 10 to 15 show successive stages in the insertion to the FIG. 3 position.
Figure 11:
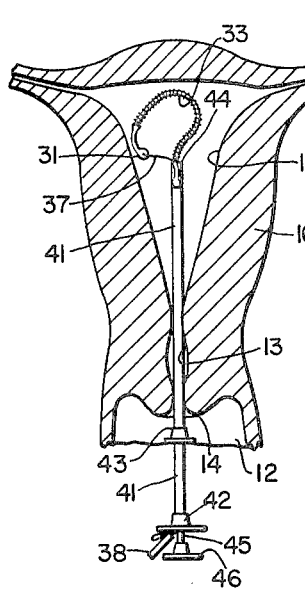
Figure 12:
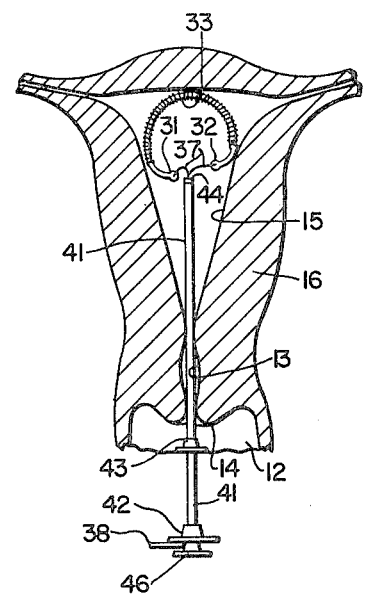
Figure 13:
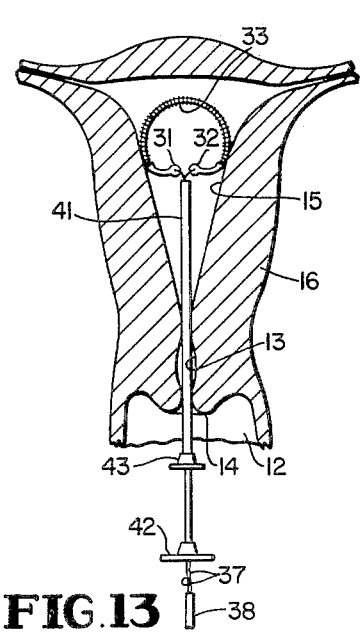
Figure 14:
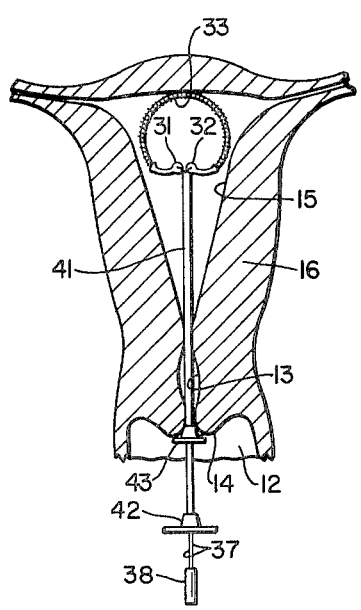
Figure 15:
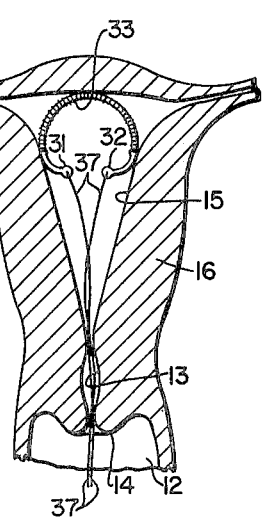

In order to insert the device in the uterine cavity of a patient, the patient is prepared and the device 20, inserter 41 and plunger 45 are removed from the pack after sounding the uterus with a uterine sound to determine the dimensions of the uterus. The flange 43 is then adjusted on the tube 41 of the inserter so that it lies about 2 cms from the anterior end 44. In this position, the end 44 will be about 2 cms. from the roof of the fundus of the uterus 16 when the flange engages the os cervix (FIG. 10). The device is then straightened and inserted into the tube of the inserter, which has an internal diameter sufficient to accommodate the device and allow the device to slide along the tube. The device is inserted with a successive lift and push motion (FIG. 9A) and is pushed with the plunger 45 to a position leaving a length of about 1 cm clear at the anterior end 44 of the inserter. The ends of the nylon threads 37 with the attached bead 38 lie outside the tube. When the inserter is fully loaded the tube tends to curve or take up a "sound like" attitude as shown in FIG. 9B. The flange 43 is at 90° to the curvature. A bi-valve vaginal speculum is inserted into the vagina, the os cervix exposed and its anterior lip grasped by a vulsellum. The loaded inserter is then passed through the vagina 12 and inserted slowly and gently through the endocervical canal with a careful "push-and-pull" motion until the flange 43 rests against the cervical os. The inserter 41 is then withdrawn about 1 cm and rotated 90°. The plunger 45, which meanwhile has been in the tube but with its finger grip spaced from that of the inserter 41, is then pushed gently into the inserter to transfer the device 20 to the uterine cavity, the nylon threads 37 being held by the bead, one of the threads controlling the motion of the first extruding head of the device after it passes out of the inserter until its connected string becomes taut and starts to pull the extruding end into a tight C-shape, as it passes into the uterine cavity (FIG. 10 and FIG. 11). When the device is wholly in the uterine cavity, the plunger 45 has reached the limit of its travel into the tube (FIG. 12). The plunger is then withdrawn from the inserter, and with the inserter 41 being held firmly in position, traction is applied to the bead attached to the nylon threads 37 to draw the heads 31 and 32 together (FIG. 13). This action assists the device in "regaining its memory" and to take up the correct operative configuration (i.e., that in which it was moulded). While the pull on the bead is being maintained, the inserter is pushed upwards once more until the flange 43 engages the os again. This action places the device 20 in its correct plane and position in the fundus (FIG. 14). The bead 38 is then cut off and discarded and the inserter is withdrawn. The threads 37 are then cut off about 3 cms. from the os.

The device is simply withdrawn from the uterus by pulling on one of the threads. The head to which the particular thread is secured passes down through the endocervical canal followed by the remainder of the device, which straightens out in order to pass from the uterus.

It will be understood that in this embodiment, X-ray scanning can be carried out since the copper provides the desired shadow on an X-ray plate. The position of the device can thus be determined.

In both embodiments, the device may be hollow (not shown) and may have means for dispensing, when in the uterus, hormonal or spermicidal chemicals. The means may be a plurality of pores extending to the boundary surface. The inserter and plunger may be made of plastics or metal.

In the device described with reference to the drawings, the copper with a surface area of 200 sq. mm or more in contact with the mucous membrane of the uterus enhances the contraceptive action of the device and diminishes the side effects of intermenstrual bleeding and pain which may follow insertion of the device. Further the presence of copper allows a smaller and more effective device to be used.

It will be understood that an IUD by its local and harmless action prevents sperm reaching the ovum and thus fertilization and conception are prevented.

It will be further understood that the wire may be zinc, an alloy, such as German Silver, or of any other suitable metal.

Although a range of 200 – 450 sq. mm has been mentioned as a preferred range for the surface area of the metal wire, it should be understood that any surface area up to 1000 sq. mm may be utilized depending on the diameter of the wire used.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. A method of inserting an intrauterine contraceptive device into the fundal region of the uterine cavity, using the device and an inserter, the device being a linear type of intrauterine contraceptive device made of flexible material comprising an elongate member which, prior to placement in the inserter and in situ, assumes a linear arch-shape wherein the two terminal portions of the linear form are connected by a non-interrupted continuous arch form, and the terminal portions curve inwardly toward each other and the member being of a material with sufficient flexibility to assume a substantially straight linear form when placed inside the inserter to accommodate insertion, and after expulsion from the inserter to assume the arched, in situ, configuration, which has dimensions substantially encompassing an area enabling the device to be contained within a normal uterus; and the inserter being a hollow tube of sufficient internal diameter to accommodate the device in its substantially straightened out configuration comprising the steps of: substantially straightening the member and inserting it into the hollow tube; inserting the tube through the cervical canal a predetermined distance whereupon the inserted end of the tube is space from the fundal roof a distance at least equal to the depth dimension of the device in its arched configuration; pushing the device from the tube into the fundal cavity; maintaining the extruding end of the device at a fixed distance, slightly spaced from the end of the hollow tube, to cause the body of the device to positively curve into the arched configuration laterally along the facing walls of the fundal cavity until the device is completely pushed from the hollow tube; positively bringing both ends of the device into close juxtaposition and shifting the device in its substantially in situ configuration to a proper location in the fundal cavity; and removing the hollow tube.

2. A method according to claim 1, wherein the inserter includes the hollow tube, a friction fitting flange slidably along the hollow tube, a unit on the tube to enable determination of rotary positioning about the axis of the tube and the tube is made from a flexible material so that the portion of the tube which carries the straightened device assumes a slight sideways curvature due to the bias of the device; wherein the distance of insertion of the hollow tube into the cervical canal is predetermined by preliminary sounding and the slidable flange is preplaced on the tube at the determined distance from the insertion end of the tube and the tube containing the device is then inserted into the cervical canal until the flange abuts the os cervix.

3. The method as defined in claim 2, wherein the slightly curved end portion of the hollow tube which contains the substantially straightened device is rotationally disposed during insertion into the cervical canal to accommodate passage of the tube along the normal curvature of the cervical canal; and following insertion of the inserter tube to the predetermined distance but prior to pushing the device from the tube rotating the tube so that the curvature is essentially aligned with theplanar cavity between facing walls of the uterine cavity.

4. The method as defined in claim 1, wherein the device has a thread secured to depend from each of its free ends and a bead engages and secures the ends of both depending threads so that the length of each depending thread measured from the associated end of the device to the bead is longer than the length of the tube by a dimension approximating the distance between the free end of the device in its arched configuration and including the step of causing the bead to abut the exterior end of the tube during the step of pushing the device from the tube.

5. The method as defined in claim 4, wherein upon complete extrusion of the device from the tube into the fundal cavity and before withdrawal of the tube, the attached threads are pulled by traction on the bead to bring the two free ends of the device into close juxtaposition while in situ.

6. The method as defined in claim 5, wherein the bead is clipped from the threads after placement of the device is obtained.

7. The method as defined in claim 5, wherein the inserter tube and the extruded device with its threads and attached bead are withdrawn a distance of approximately 1 cm before drawing the free ends of the device together by traction of the bead, and then, with the free ends drawn together at the end of the inserter tube, pushing the inserter and device into the uterus until the flange again engages the os cervix whereby the device rests in the fundal region of the uterus in a correct plane and position.

* * * * *